(12) United States Patent
Baier et al.

(10) Patent No.: US 10,758,504 B2
(45) Date of Patent: Sep. 1, 2020

(54) COMPOSITIONS AND METHODS OF USE OF β-HYDROXY-β-METHYLBUTYRATE (HMB) FOR ENHANCING RECOVERY FROM SOFT TISSUE TRAUMA

(71) Applicant: Metabolic Technologies, Inc., Ames, IA (US)

(72) Inventors: Shawn Baier, Polk City, IA (US); Naji Abumrad, Nashville, IA (US); Emily Harris, Des Moines, IA (US)

(73) Assignee: Metabolic Technologies, Inc., Ames, IA (US)

( * ) Notice: Subject to any disclaimer, the term of this patent is extended or adjusted under 35 U.S.C. 154(b) by 146 days.

(21) Appl. No.: 15/267,717

(22) Filed: Sep. 16, 2016

(65) Prior Publication Data

US 2017/0071886 A1    Mar. 16, 2017

Related U.S. Application Data

(60) Provisional application No. 62/219,208, filed on Sep. 16, 2015.

(51) Int. Cl.
*A61K 31/19* (2006.01)
*A61P 19/04* (2006.01)
*A61P 21/00* (2006.01)

(52) U.S. Cl.
CPC .............. *A61K 31/19* (2013.01); *A61P 19/04* (2018.01); *A61P 21/00* (2018.01)

(58) Field of Classification Search
CPC ........... A61K 31/19; A61P 19/04; A61P 21/00
See application file for complete search history.

(56) References Cited

U.S. PATENT DOCUMENTS

| | | | |
|---|---|---|---|
| 4,462,988 A | 7/1984 | Arias-Alvarez | |
| 4,992,470 A | 2/1991 | Nissen | |
| 5,028,440 A | 7/1991 | Nissen | |
| 5,084,742 A | 2/1992 | Nissen | |
| 5,348,979 A * | 9/1994 | Nissen | A61K 31/19 426/2 |
| 5,360,613 A | 11/1994 | Nissen | |
| 5,556,645 A * | 9/1996 | Bockman | A61K 9/7023 424/650 |
| 5,756,469 A | 5/1998 | Beale | |
| 6,031,000 A | 2/2000 | Nissen et al. | |
| 6,103,764 A | 8/2000 | Nissen | |
| 6,291,525 B1 | 9/2001 | Nissen | |
| 8,217,077 B2 | 7/2012 | Baxter et al. | |
| 2004/0071825 A1 | 4/2004 | Lockwood | |
| 2004/0132603 A1 * | 7/2004 | Narhi | A61L 27/306 501/63 |
| 2004/0253295 A1 | 12/2004 | Martin et al. | |
| 2005/0215640 A1 | 9/2005 | Baxter et al. | |
| 2006/0003947 A1 | 1/2006 | Udell | |
| 2007/0142469 A1 | 6/2007 | Thomas et al. | |
| 2011/0256297 A1 * | 10/2011 | Johns | A23L 27/86 426/583 |
| 2013/0017283 A1 * | 1/2013 | Zemel et al. | A61K 36/87 424/766 |
| 2014/0171854 A1 | 6/2014 | Jacofsky et al. | |

FOREIGN PATENT DOCUMENTS

| | | | |
|---|---|---|---|
| WO | WO-2006062424 A2 * | 6/2006 | ............ A61K 31/19 |
| WO | 2008024456 | 2/2008 | |
| WO | 2011075741 A1 | 6/2011 | |

OTHER PUBLICATIONS

Williams et. al., Annals of Surgery, 2002, Lippincott Williams & Wilkins, vol. 236(3), pp. 369-375.*
Merriam Webster online Medical Dictionary, accessed Sep. 6, 2018, https://www.merriam-webster.com/medical/chondral (Year: 2018).*
Elsayes et. al., Current Probl. Diagn. Radiol., Sep./Oct. 2006, pp. 206-212 (Year: 2006).*
Merriam-Webster, definition of "trauma", https://www.merriam-webster.com/dictionary/trauma, retrieved on Mar. 4, 2019 (Year: 2019).*
"Juven, Abbott Nutrition", "http://web.archive.org/web/20150316183819/http://abbottnutrition.com/brands/products/juven", Mar. 16, 2015, Publisher: Abbott Nutrition.
"Juven Nutritional Drinks, PR02Nutrition", "http://web.archive.org/web/20 150513161825/http://www.pr02nutrition.comljuven.html>. entire 4,6,9,11-21", May 13, 2015, pp. 1-4, Publisher: Juven—PRO2Nutrition.
Krebs, H. A. & Lund, P., "Aspects of the regulation of the metabolism of branched-chain amino acids.", "Advan. Enzyme Regul.", Jan. 1, 1977, pp. 375-394, vol. 15.
Krebs et al., "Moderate exercise improves gait stability in disabled elders.", "Arch. Phys. Med. Rehabil.", Jan. 1, 1998, pp. 1489-1495, vol. 79.
Kreider et al, "Effects of calcium beta-hydroxy-beta-methylbutyrate (HMB) supplementation during resistance-training on markers of catabolism, body composition and strength.", "Int J Sports Med", Jan. 1, 1999, pp. 503-509, vol. 20.
McAllan et al., "The efficiency of microbial protein synthesis in the rumen and the degradability of feed nitrogen between the mouth and abomasum in steers given different diets", "Br. J. Nutr", Jan. 1, 1984, pp. 77-83, vol. 51.
McCarty et al., "Toward a Core Nutraceutical Program for Cancer Management", Jan. 1, 2006, pp. 150-171, vol. 5, No. 2.

(Continued)

*Primary Examiner* — Sarah Pihonak

(74) *Attorney, Agent, or Firm* — Davis, Brown, Koehn, Shors & Roberts, P.C.; Emily E. Harris

(57) ABSTRACT

The present invention provides a composition comprising HMB. Methods of administering HMB to an animal are also described. HMB is administered to enhance recovery from soft tissue trauma, including both acute and non-acute soft tissue trauma. Enhanced recovery includes reduced recovery time and enhanced soft tissue healing.

21 Claims, 1 Drawing Sheet

(56) References Cited

OTHER PUBLICATIONS

Menconi, M., Gonnella, P., Petkova, V., Lecker, S. & Hasselgren, P. O, "Dexamethasone and corticosterone induce similar, but not identical, muscle wasting responses in cultured L6 and C2C12 myotubes.", Jan. 1, 2008, pp. 353-364, vol. 105, Publisher: J Cell Biochem.

Morelli et al., "1,25(OH)2-vitamin D3 stimulation ofphospholipases C and D in muscle cells involves extracellular calcium and a pertussis-sensitive G protein.", "Mol. Cell Endocrinol.", Jan. 1, 1996, pp. 207-211, vol. 122.

Nemere et al, "Identification of a specific binding protein for 1 alpha,25-dihydroxyvitamin 03 in basal-lateral membranes of chick intestinal epithelium andrelationship to transcaltachia", Jan. 1, 1994, pp. 23750-23756, vol. 269, Publisher: J. Biol. Chem.

Nieuwenhuijzen Kruseman, A. C., Van Der Klauv, M. M. & Pijpers, E., "Hormonal and metabolic causes of muscular weakness and the increased risk of fractures in elderly people", Jan. 1, 2005, pp. 1033-1037, vol. 149, Publisher: Ned. Tijdschr. Geneeskd.

Nissen et al., "Analysis of beta-hydroxy-beta-methyl butyrate in plasma by gas chromatography and mass spectrometry.", "Anal. Biochem", Jan. 1, 1990, pp. 17-19, vol. 188.

Nissen et al., "beta-Hydroxy-beta-methylbutyrate (HMB) supplementation in humans is safe and may decrease cardiovascular risk factors", "J Nutr", Jan. 1, 2000, pp. 1937-1945, vol. 130.

Nissen, "Effect of dietary supplements on lean mass and strength gains with resistance exercise: a meta-analysis", "J Appl. Physiol", Jan. 1, 2003, pp. 651-659, vol. 94.

Nissen et al., "The effect of the leucine metabolite beta-hydroxy beta-methylbutyrate on muscle metabolism during resistance- excersise training", "J. Appl. Physiol", Jan. 1, 1996, pp. 2095-2104, vol. 81, No. 5.

Nissen et al., "Nutritional role of the leucine metabolite beta-hydroxy-beta-methylbutyrate (HMB).", "J. Nutr. Biochem", Jan. 1, 1997, pp. 300-311, vol. 8.

Ostaszewski et al., "The leucine metabolite 3-hydroxy-3-methylbutyrate (HMB) modifies protein turnover in muscles of the laboratory rats and domestic chicken in vitro.", "J. Anim. Physiol. Anim. Nutr.", Jan. 1, 2000, pp. 1-8, vol. 84.

Panton et al., "Nutritional supplementation of the leucine metabolite beta-hydroxy beta-methylbutyrate (HMB) during resistance training", "Nutr.", Jan. 1, 2000, pp. 734-739, vol. 16, No. 9.

Plaut et al., "Enzymatic incorporation of C14-bicarbonate into acetoacetate in the presence of various substrates.", "J. Biol. Chem.", Jan. 1, 1951, pp. 435-445, vol. 192.

Rabinowitz et al., "Branched chain acids in the biosynthesis of squalene and cholesterol.", "Fed. Proc", Jan. 1, 1955, pp. 760-761, vol. 14.

Rathmacher et al., "The effect of the leucine metabolite beta-hydroxy-beta-methylbutyrate on lean body mass and muscle strength during prolonged bed res!.", "FASEB", Jan. 1, 2001, p. A909, vol. 13.

Rathmacher et al., "Supplementation with a combination of beta-hydroxy-beta-methylbutyrate (HMB), arginine, and glutamine is safe and could improve hematological parameters", "JPEN J Parenter Enteral Nutr", Jan. 1, 2004, pp. 65-75, vol. 28.

Robinson et al., "Enzymatic carbon dioxide fixation by senecioyl coenzyme", "A Fed. Proc", Jan. 1, 1954, p. 281 vol. 13.

Rogers, "Effects of dumbbell and elastic band training on physical function in older inner-city African-American women", "Women Health", Jan. 1, 2002, pp. 33-41, vol. 36.

Rudney et al., "Biosynthesis of branched chain acids", "Fed. Proc.", Sep. 1, 1955, pp. 757-759.

Rudney, "The synthesis of beta-hydroxy-beta-methylglutaric acid in rat liver homogenates", "J. Am. Chem. Soc", Jan. 1, 1954, p. 2595 vol. 76.

Sanchez et al, "1,25-Dihydroxyvitamin D3 administration to 6-hydroxydopamine-lesioned rats increases glial cell line-derived neurotrophic factor and partially restores tyrosine hydroxylase expression in substantia nigra and striatum", "J Neurosci. Res", Jan. 1, 2009, pp. 723-732., vol. 87.

Sato et al, "low-dose vitamin D prevents muscular atrophy and reduces falls and hip fractures in women after stroke: a randomized controlled trial.", Jan. 1, 2005, pp. 187-192, vol. 20, Publisher: Cerebrovasc. Dis.

Selles et al., "Rapid stimulation of calcium uptake and protein phosphorylation in isolated cardiac muscle by 1 ,25-dihydroxyvitamin D3.", "Mol. Cell Endocrinol", Jan. 1, 1991, pp. 67-73, vol. 77.

Simpson et al, "Identification of 1,25-dihydroxyvitamin 03 receptors and activities in muscle", Jan. 1, 1985, pp. 8882-8891, vol. 260, Publisher: J. Biol. Chem.

Slater et al., "beta-hydroxy beta-methylbutyrate (HMB) supplementation does not affect changes in strength or body composition during resistancE D", "In!. J. Sport Nutr. Exerc. Metab", Jan. 1, 2001, pp. 384-396, vol. 11.

Smith et al., "Attenuation of proteasome-induced proteolysis in skeletal muscle by b-hydroxy-b-methylbutyrate in cancer-induced muscle loss", "Cancer Research", Jan. 1, 2005, pp. 277-283, vol. 65.

Smith et al., "Mechanism of the attenuation of proteolysis-inducing factor stimulated protein degradation in muscle by beta-hydroxy-beta-methylbutyrate", "Cancer Res", Jan. 1, 2004, pp. 8731-8735, vol. 64.

Snijder et al., "Vitamin 0 status in relation to one-year risk of recurrent falling in older men and women.", Jan. 1, 2006, pp. 2980-2985, vol. 91, Publisher: J. Clin. Endocrinol. Metab.

Somjen, D., Weisman, Y., Kohen, F., Gayer, B., Limor, R., Sharon, 0., Jaccard, N., Knoll, E. & Stern, N., "25-hydroxyvitamin D3-1alpha-hydroxylase is expressed in human vascular smooth muscle cells and is upregulated by D", Jan. 1, 2005, pp. 1666-1671, vol. 111, Publisher: Circulation.

Vazquez et al., "1 alpha,25-(OH)2-vitamin D3 stimulates the adenylyl cyclasepathway in muscle cells by a GTP-dependent mechanism which presumably involves phosphorylation of G alpha i.", "Biochem. Biophys. Res. Commun.", Jan. 1, 1997, pp. 125-128, vol. 234.

Vieth et al., "The urgent need to recommend an intake of vitamin 0 that is effective", Jan. 1, 2007, pp. 649-650, vol. 85, Publisher: Am. J. D Clin. Nutr.

Vukovich et al., "Body composition in 70-year old adults responds to dietary beta-hydroxy-beta-methylbutyrate (HMB) similar to that of young adults", "J. Nutr", Jan. 1, 2001, pp. 2049-2052, vol. 131, No. 7.

Wicherts et al., "Vitamin o status predicts physical performance and its decline in older persons", Jan. 1, 2007, pp. 2058-2065, vol. 92, Publisher: J. Clin. Endocrinol. Metab.

Wu et al., "p38 and extracellular signal-regulated kinases regulate the myogenic program at multiple steps.", "Mol. Cell Biol", Jan. 1, 2000, pp. 3951-3964, vol. 20.

Xu, H., McCann, M., Zhang, Z., Posner, G. H., Bingham, V., Ei-Tanani, M. & Campbell, F. C., "Vitamin D receptor modulates the neoplastic phenotype through antagonistic growth regulatory signals.", "Mol. Carcinog.", Jan. 1, 2009, pp. 758-772, vol. 48.

Zabin et al., "The utilization of butyric acid for the synthesis of cholesterol and fatty acids", "J. Biol. Chem", Jan. 1, 1951, pp. 261-266, vol. 192.

Zanello et al., "cDNA sequence identity of a vitamin D-dependent calcium binding protein in the chick to calbindin D-9K.", "Endocrinology", Jan. 1, 1995, pp. 2784-2787, vol. 136.

Zehnder, D., Bland, R., Williams, M. C., McNinch, R. W., Howie, A. J., Stewart, P. M. & Hewison, M., "Extrarenal expression of 25-hydroxyvitamin d(3)-1 alpha-hydroxylase", "J. Clin. Endocrinol. Metab", Jan. 1, 2001, pp. 888-894, vol. 86.

Zion et al., "home-based resistance-training program using elastic bands for elderly patients with orthostatic hypotension.", "Clin. Auton. Res", Jan. 1, 2003, pp. 286-292, vol. 13.

Laboratorium DermaPharm, "Dog Vital nutritious supplement with HMB for dogs." http://www.dermapharm.com.pl/en/o/Dog-Vital-nutritious-supplement-with-HMB-for-dogs 2014.

Laboratorium DermaPharm, "Flawitol with HMB for active dogs." http://www.dermapharm.com.pl/en/o/Flawitol-z-HMB-dla-psow-aktywnych 2014.

(56) References Cited

OTHER PUBLICATIONS

Adamson et al., "The significance of certain carboxylic acids as intermediates in the biosynthesis of cholesterol.", "Biochim. Biophys Acta", Jan. 1, 1957, pp. 472-479., vol. 23.
Bachhawat et al., "The enzymatic cleavage of beta-hydroxy-beta-methylglutaryl coenzyme a to aceto-acetate and acetyl coenzyme", "A. J. Biol. Chem", Jan. 1, 1955, pp. 727-736, vol. 216.
Baier et al., "Year-long changes in lean body mass in elderly men and women supplemented with a nutritional cocktail of beta-hydroxy-beta-methylbutyrate (HMB), arginine, and lysine", "JPEN", Jan. 1, 2009, pp. 71-82, vol. 33.
Birge et al., "25-hydroxycholecalciferol stimulation of muscle metabolism.", Jan. 1, 1975, pp. 1100-1107, vol. 56, Publisher: J. Clin. Invest.
Birge et al., "25-hydroxycholecalciferol stimulation of muscle metabolism", "J. Clin. Invest", Jan. 1, 1975, pp. 1100-1107, vol. 56.
Bischoff et al., "Effects of vitamin 0 and calcium supplementation on falls: a randomized controlled trial.", Jan. 1, 2003, pp. 343-351, vol. 18, Publisher: J. Bone Miner. Res.
Bischoff et al., "Estimation of optimal serum concentrations of 25-hydroxyvitamin 0 for multiple health outcomes.", Jan. 1, 2006, pp. 18-28, vol. 84, Publisher: Am. J. Clin. Nutr.
Bischoff et al., "In situ detection of 1, 25-dihydroxyvitamin 03 receptor in human skeletal muscle tissue", "Histochem.", Jan. 1, 2001, pp. 19-24, vol. 33.
Bischoff-Ferrari, H. A., Borchers, M., Gudat, F., Durmuller, U., Stahelin, H. B. & Dick, W., "Vitamin D receptor expression in human muscle tissue decreases with age.", "J. Bone Miner. Res.", Jan. 1, 2004, pp. 265-269, vol. 19.
Bloch et al., "Utilization of branched chain acids in cholesterol synthesis", "J. Biol. Chem", Jan. 1, 1954, pp. 687-699, vol. 211.
Boland et al., "Avian muscle cells as targets for the secosteroid hormone 1,25-dihydroxy-vitamin 03", Jan. 1, 1995, pp. 1-8, vol. 114, Publisher: Mol. Cell Endocrinol.
Boland et al., "nongenomic stimulation of tyrosine phosphorylation cascades by 1 ,25(OH)(2)D(3) by VDR-dependent and -independent mechanisms in muscle cells", "Steroids", Jan. 1, 2002, pp. 477-482, vol. 67.
Boland et al., "Presence of a 1,25-dihydroxy-vitamin 03 receptor in chick skeletal muscle myoblasts.", Jan. 1, 1985, pp. 305-311, vol. 128, Publisher: Biochem. Biophys. Res. Commun.
Boland, "Role of vitamin 0 in skeletal muscle function", Jan. 1, 1986, pp. 434-448, vol. 7, Publisher: Endocr. Rev.
Burne et al., "Behavioural characterization of vitamin 0 receptor knockout mice.", "Behav. Brain Res.", Jan. 1, 2005, pp. 299-308, vol. 157.
Capiati et al., "1 ,25(OH)2-vitamin 03 induces translocation of the vitamin 0 receptor (VDR) to the plasma membrane in skeletal muscle cells", Jan. 1, 2002, pp. 128-135, vol. 86, Publisher: J. Cell Biochem.
Clark et al., "Nutritional treatment for acquired immunodeficiency virus-associated wasting using beta-hydroxy-beta-methylbutyrate, glutamine and arginine: A randomized, double-blind, placebo-controlled study", "JPEN J Parenter Enteral Nutr", Jan. 1, 2000, pp. 133-139, vol. 24, No. 3.
Coon, "Enzymatic synthesis of branched chain acids from amino acids.", "Fed. Proc", Jan. 1, 1955, pp. 762-764, vol. 14.
Cornet et al., "1,25-Dihydroxyvitamin D3 regulates the expression of VDR and NGF gene in Schwann cells in vitro", "J Neurosci. Res", Jan. 1, 1998, pp. 742-746, vol. 53.
Costa et al., "1,25-dihydroxyvitamin D3 receptors and hormonal responses in cloned human skeletal muscle cells.", "Endocrinology", Jan. 1, 1986, pp. 2214-2220, vol. 119.
Deboland, "In vitro cellular muscle calcium metabolism. Characterization of effects of 1,25- dihydroxy-vitamin 03 and 25-hydroxy-vitamin 03.", "Z. Naturforsch", Jan. 1, 1985, pp. 102-108, vol. 40.
Deluca, "The vitamin 0 story: a collaborative effort of basic science and clinical medicine", "FASEB", Jan. 1, 1988, pp. 224-236.
Deluca, "The vitamin D story: a collaborative effort of basic science and clinical medicine.", "FASEB", Jan. 1, 1988, pp. 224-236, vol. 2.
Eley et al., "Attenuation of depression of muscle protein synthesis induced by lipopolysaccharide, tumor necrosis factor and angiotensin II by beta-hydroxy-beta-methylbutyrate", "Am. J. Physiol D", Jan. 1, 2008, pp. E1409-E1416., vol. 295.
Eley et al., "Mechanism of Attenuation of Muscle Protein Degradation Induced by Tumor Necrosis Factor Alpha and Angiotensin II by beta-Hydroxy-beta-methylbutyrate", "Am J Physiol Endocrinol", Oct. 7, 2008, vol. 295.
Eley et al., "Signaling pathways initiated by b-hydroxy-b-methylbutyrate to attenuate the depression of protein synthesis in skeletal muscle in response to cachectic stimuli", "Am J Physiol Endocrinol Metab", Jul. 3, 2007, pp. E923-E931, vol. 293.
Eubanks et al., "Reversal of cancer-related wasting using oral supplementation with a combination of beta-hydroxy-beta-methylbutyrate, arginine, and glutamine", "Am. J. Surg", Jan. 1, 2002, pp. 471-479, vol. 183.
Freedman, "Transcriptional targets of the vitamin 03 receptor-mediating cell cycle arrest and differentiation", "J. Nutr.", Jan. 1, 1999, pp. 581S-586S, vol. 129.
Frexes-Steed, "Role of insulin and branched-chain amino acids in regulating protein metabolism during fasting.", "Endocrinol. Metab", Jan. 1, 1990, pp. E907-E917, vol. 258, Publisher: Am. J. Physiol.
Fuller, J. C., Jr., Nissen, S. L. & Huiatt, T. W., "Use of 180-labelled leucine and phenylalanine to measure protein turnover in muscle cell cultures and possible futile cycling during aminoacylation.", Jan. 1, 1993, pp. 427-433, vol. 294, Publisher: Biochem.J.
Gallagher et al., "beta-Hydroxy-beta- methylbutyrate ingestion, Part I: Effects on strength and fat free mass.", "Med Sci Sports Exerc", Jan. 1, 2000, pp. 2109-2115, vol. 32, No. 12.
Gallagher et al., "beta-Hydroxy-beta-methylbutyrate ingestion, Part II: Effects on hematology, hepatic, and renal function.", "Med Sci Sports Exerc", Jan. 1, 2000, pp. 2116-2119, vol. 32, No. 12.
Gey et al., "The influence of isoperenic C5 and C6 compounds upon the acetate incorporation into cholesterol.", "Helvetica Chim. Acta", Jan. 1, 1957, pp. 2354-2368, vol. 40.
Gey et al., "Influence of iosoprenoid C5 and C6 compounds on the incorporation of acetate in cholesterol.", "Helvetica Chim. Acta", Jan. 1, 1957, pp. 23542-368, vol. 40.
Gniadecki, R., Gajkowska, B. & Hansen, M., "1,25-dihydroxyvitamin D3 stimulates the assembly of adherens functions in keratinocytes: involvement of protein kinase", "Endocrinology", Jan. 1, 1997, pp. 2241-2248, vol. 138.
Haddad et al., "25-Hydroxycholecalciferol: specific binding by rachitic tissue extracts", Jan. 1, 1971, pp. 829-834, vol. 45, Publisher: Biochem. Biophys Res Commun.
Haddad et al., "Widespread, specific binding of 25-hydroxycholecalciferol in rat tissues.", Jan. 1, 1975, pp. 299-303, vol. 250, Publisher: J Biol Chem.
Harper et al., "Effects of ingestion of disproportionate amounts of amino acids", "Physiol. Rev", Jan. 1, 1970, pp. 428-558, vol. 53.
Heaney et al., "Calcium absorption varies within the reference range for serum 25-hydroxyvitamin D", "J. Am. Coil. Nutr", Jan. 1, 2003, pp. 142146, vol. 22.
Heaney, "Vitamin D in Health and Disease", "Clin. J. Am. Soc. Nephrol", Jan. 1, 2008, pp. 1535-1541, vol. 3.
Heaney, "Vitamin D endocrine physiology", "J. Bone Miner. Res", Jan. 1, 2007, pp. V25-V27., vol. 2.
Heislein et al., "A strength training program for postmenopausal women: a pilot study", "Arch. Phys. Med. Rehabil", Jan. 1, 1994, pp. 198-204, vol. 75.
Holick et al., "[Hormonal and metabolic causes of muscular weakness and the increased risk of fractures in elderly people", "Ned. Tijdschr", Jan. 1, 2005, pp. 1033-1037, vol. 149.
Holick, "Vitamin D deficiency", "N. Engl. J. Med", Jan. 1, 2007, pp. 266-281, vol. 357.
Isler et al., "Biosynthesis of cholesterol from beta,t-dihydroxy-beta-methylvaleric acid", "Helvetica Chim. Acta", Jan. 1, 1957, pp. 2369-2373., vol. 40.
Jones, G., "Expanding role for vitamin D in chronic kidney disease: importance of blood 25-0H-D levels andextra-renal 1 alpha-

(56) References Cited

OTHER PUBLICATIONS hydroxylase in the classical and nonclassical actions of 1alpha,25-dihydroxyvitamin D", "Semin. Dial", Jan. 1, 2007, pp. 316-324, vol. 20.
Jowko et al., "Creatine and beta-hydroxy-beta-methylbutyrate (HMB) additively increase lean body mass and muscle strength during a weight-training program", "Nutrition", 2001, pp. 558-566, vol. 17.
Knitter et al., "Effects of beta-hyroxy-methylbutyrate on muscle damage following a prolonged run", "J Appl. Physiol", Jan. 1, 2000, pp. 1340-1344, vol. 89, No. 4.
Advertisement, "Delivering High Levels of HMB glutamine and lactoterrin", "High Performance Series", Publisher: MET RX.
Associated Press, "Disfiguring Fat Adds to Aids Misery", Jan. 1, 1998, Publisher: Associated Press.
Barbul, "Arginine: Biochemistry, Physiology, and Therapeutic Implications", "Journal of Parenteral and Enteral Nutrition", Jan. 1, 1986, vol. 10, No. 2, Publisher: American Society for Parenteral and En. Nutrition.
Clark et al., "Effect of an amino acid mixtrue containing HMB in HIV related wasting", "12th World AIDS Conference", Jun. 1, 1998, Published in: Geneva.
Daly et al., "Enteral nutrition with supplemental arginine RNA and omega 3 fatty acids in patients after operation: immunologic metabolic and clinical outcome", "Surgery", Jul. 1, 1992, pp. 56-67, vol. 11, No. 1, Publisher: PubMed.
Hammarqvist et al., "Glutamine in surgical nutrition and metabolism", "Amino Acids in Critical Care and Cancer", Jan. 1, 1994, pp. 27-44, Publisher: RG Landes Co.
Advertisement, "HPS Met—RX", "High Performance Series", , Publisher: MET RX.
Advertisement, "Met-RX engineered nutrition", "High Performance Series", , Publisher: MET RX.
Advertisement, "Take your nutrition to new levels of performance", , Publisher. MET RX.
Advertisement, "MET-RX engineered nutrition Anabolic Drive", , Publisher: MET RX.
Global Reach, "MTI-AIDS NCMC001—Study Outline", , Publisher: Global Reach.

Neu et al., "Glutamine nutrition and metabolism: where do we go from here?", "FASEB Journal", Jun. 1, 1996, pp. 829-837, vol. 10.
Pichard et al., "Randomized double-bline controlled study of 6 months of oral nutritional supplementation with arginine and omega 3 fattyacids in HIV infected patients", "AIDS", Jan. 1, 1998, pp. 53-63, vol. 12, No. 1, Publisher: PubMed.
Sousa et al., "Calcium b-hydroxy-b-methylbutyrate. Potential role as a phosphate binder in uremia", "Nephron", 1996, pp. 391-394, vol. 72, Publisher: Karger.
Suttmann et al., "Weight gain and increased concentrations of receptor proteins for tumor necrosis factor after patients with symptomatic HIV infections received fortified nutrition support", "J Am Diet Assoc", Jun. 1, 1996, pp. 565-569, vol. 6, No. 6, Publisher: PubMed.
Torosian, "Arginine in nutrition and surgery: current status and potential", "Amino Acids in Critical Care and Cancer", Jan. 1, 1994, pp. 45-52, Publisher RG Landes Co.
MET RX, "Met- Rx High performance series discover a whole new training regimen", , Publisher: MET RX.
Advertisement, "Twinlab—GrowthFuel", , Publisher: Twin Lab.
Advertisement, "Twinlab anti-catabolic HMB fuel plus", , Publisher: Twin Lab.
Advertisement, "We know your sports nutrition customers", , Publisher: Twin Lab.
Kuhls et al., "Beta-Hydroxy-Beta-Methylbutyrate Supplementation in Critically III Trauma Patients", "Journal of Trauma Injury, Infection, and Critical Care", 2007, pp. 125-131, vol. 62, No. 1.
Kusabbi et al., "Effects of the Oral Nutritional Supplement Containing Arginine, Glutamine, and Hydroxymethylbutyrate (Abound) on Healing of Colonic Anastomoses in Rats", "Indian Journal of Surgery", Apr. 14, 2015, pp. 1242-1247, vol. 77, No. 3.
Williams et al., "Effect of a Specialized Amino Acid Mixture on Human Collagen Deposition", "Annals of Surgery", 2002, pp. 369-375, vol. 236, No. 3.
Wilson et al., "Beta-Hydroxy-Beta-Methylbutyrate free acid reduces markers of exercise-induced muscle damage and impoves recovery in resistance-trained men", "British Journal of Nutrition", 2013, pp. 538-544, vol. 110.

\* cited by examiner

COMPOSITIONS AND METHODS OF USE OF β-HYDROXY-β-METHYLBUTYRATE (HMB) FOR ENHANCING RECOVERY FROM SOFT TISSUE TRAUMA

This application claims priority to U.S. Provisional Patent Application No. 62/219,208 filed Sep. 16, 2015 and herein incorporates the provisional application by reference.

BACKGROUND OF THE INVENTION

1. Field

The present invention relates to a composition comprising β-hydroxy-β-methylbutyrate (HMB) and methods of using HMB to enhance soft tissue healing and/or reduce recovery time from soft tissue trauma.

2. Background

Recovery of an animal from soft tissue trauma, including injuries to muscles, tendons and ligaments, typically requires significant time and cost. Acute soft tissue injury can occur during sports or physical activity or during simple everyday activities. Acute soft tissue trauma also includes the trauma that occurs during a surgical procedure, either related to repair of a soft tissue injury or unrelated to any injury and instead a result of cutting and/or manipulating soft tissue as part of any surgical procedure. Non-acute tissue injuries, such as sprains, also often require lengthy periods of rehabilitation and recovery. Even with appropriate supervision by a medical professional, healing of soft tissues can take a prolonged amount of time. These injuries can lead to delays in returning to regular activity and long-term weakness.

Soft tissue damage sustained from trauma, surgical procedures and falls are associated with increased morbidity and mortality in older adults. Recovery from soft tissue injuries often includes exercise and physical therapy and recovery may take six months or even more. Prolonged treatment is expensive and time-consuming. There is a need for a nutritional supplement to reduce recovery times, enhance soft tissue healing and enhance recovery after soft tissue trauma.

Animals such as horses, dogs and cats frequently sustain soft tissue trauma. By way of non-limiting example, it is very common for dogs to have soft tissue injuries that require surgical repair. Cruciate ligament surgeries such as TPLO (tibial-plateau-leveling osteotomy) or TTA (Tibial Tuberosity Advancement) surgery, hip replacements, and ruptured disc surgeries are commonly performed on animals. Recovery from these injuries and/or surgeries are difficult for both the pet and the owner. Owners typically have to assist the pet during walking and climbing stairs for weeks or months after surgery. Thus, the need exists for nutritional supplement that reduces the amount of time that the owner must assist the pet by days or weeks.

Alpha-ketoisocaproate (KIC) is the first major and active metabolite of leucine. A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting. HMB, combined with glutamine and arginine, has been found to increase wound collagen accumulation and improve skin wound repair.

The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB and this account for approximately 5% of leucine oxidation. HMB is superior to leucine in enhancing muscle mass and strength. The optimal effects of HMB can be achieved at 3.0 grams per day when given as calcium salt of HMB, or 0.038 g/kg of body weight per day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use. Numerous studies have shown an effective dose of HMB to be 3.0 grams per day as CaHMB (calcium HMB) (~38 mg/kg body weight-day$^{-1}$). This dosage increases muscle mass and strength gains associated with resistance training, while minimizing muscle damage associated with strenuous exercise. HMB has been tested for safety, showing no side effects in healthy young or old adults. HMB in combination with L-arginine and L-glutamine has also been shown to be safe when supplemented to AIDS and cancer patients.

Recently, HMB free acid, a new delivery form of HMB, has been developed. This new delivery form has been shown to be absorbed quicker and have greater tissue clearance than CaHMB. The new delivery form is described in U.S. Patent Publication Serial No. 20120053240 which is herein incorporated by reference in its entirety.

While it is known that HMB supplementation can also prevent or lessen muscle loss during long periods of inactivity, such as hospitalization, prior to the present invention it was unknown that administration of HMB to a mammal with soft tissue trauma, whether from acute injury such as a soft tissue tear or rupture or surgery or non-acute soft tissue damage, results in faster repair and/or recovery of the soft tissue trauma and enhanced recovery from the injury or surgery.

The present invention comprises a composition of HMB and methods of use of HMB to result in enhanced recovery from soft tissue trauma. The enhanced recovery can include enhanced soft tissue healing subsequent to trauma or injury, including the soft tissue trauma that results from surgical procedures. The enhanced recovery also includes a more rapid recovery than expected. The present invention comprises a composition of HMB and methods of use of HMB to result in soft tissue repair and regeneration subsequent to soft tissue trauma or injury, including the soft tissue trauma that results from surgical procedures.

SUMMARY OF THE INVENTION

One object of the present invention is to provide a composition for use reducing the recovery time after incurring soft tissue trauma.

A further object of the present invention is to provide a composition for use in enhancing the recovery after incurring soft tissue trauma.

Another object of the present invention is to provide a composition to enhance soft tissue healing subsequent to soft tissue injury.

An additional object of the present invention is to provide a composition for use in repair and regeneration of soft tissue subsequent to soft tissue injury.

Another object of the present invention is to provide methods of administering a composition for use reducing the recovery time after incurring soft tissue trauma.

An additional object of the present invention is to provide methods of administering a composition for use in enhancing recovery after incurring soft tissue trauma.

Another object of the present invention is to provide methods of administering a composition for use enhancing soft tissue healing subsequent to soft tissue injury.

An additional object of the present invention is to provide methods of administering a composition for use in repair and regeneration of soft tissue healing subsequent to soft tissue injury.

These and other objects of the present invention will become apparent to those skilled in the art upon reference to the following specification, drawings, and claims.

The present invention intends to overcome the difficulties encountered heretofore. To that end, a composition comprising HMB is provided. The composition is administered to a subject in need thereof. All methods comprise administering to the animal HMB. The subjects included in this invention include humans and non-human mammals.

DETAILED DESCRIPTION OF THE INVENTION

Figure 1:
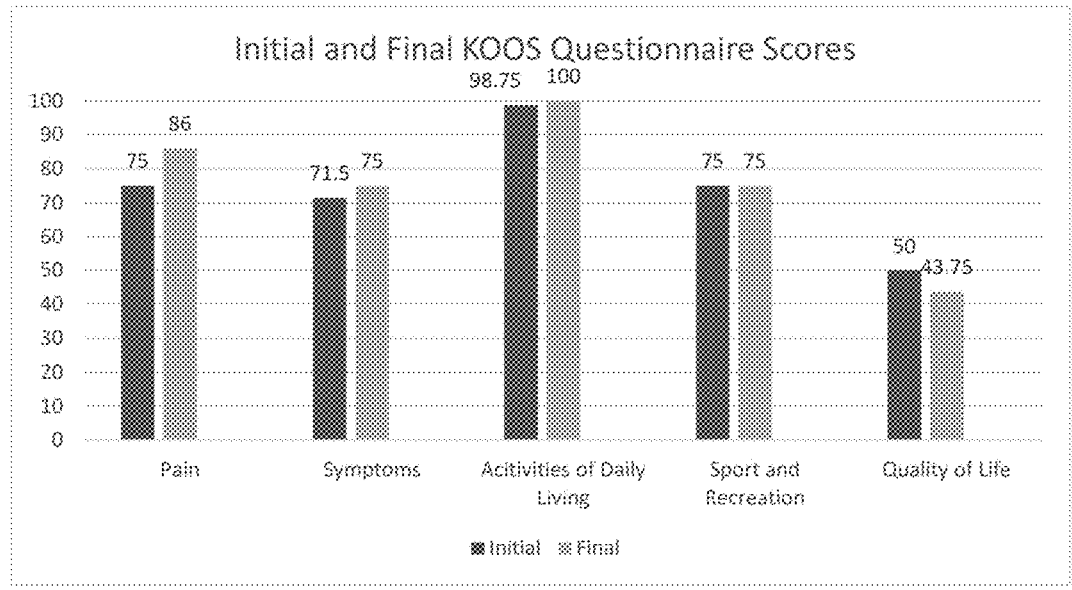
FIG. 1 is a graph depicting the initial and final KOOS Questionnaire Scores for the female subject.

It has been surprisingly and unexpectedly discovered that HMB enhances recovery from soft tissue trauma, including but not limited to reducing the recovery time after soft tissue trauma and enhancing healing of soft tissue. HMB supplementation repairs and regenerates soft tissue, resulting in enhanced recovery from soft tissue trauma. The present invention comprises a composition of HMB and methods of use of HMB to result enhanced recovery after soft tissue trauma, reducing the recovery time after soft tissue trauma, and enhanced and/or improving soft tissue healing after soft tissue trauma. In one embodiment, administration of HMB to an animal with soft tissue trauma results in a shortened time of physical therapy to substantially recover from the trauma than would be expected or the need for physical therapy may be eliminated.

HMB has been known to lessen or reverse muscle wasting following prolonged periods of inactivity, such as bed rest following surgery. It is also known that HMB can aid in wound collagen accumulation and skin repair. Prior to the present invention, however, it was unknown that HMB can enhance recovery after soft tissue trauma, including by reducing the recovery time following soft tissue injury.

This composition can be used on all age groups seeking enhanced recovery following soft tissue trauma, from infants, children and teens to the elderly and every age in between. This composition can also be used in humans and non-human mammals such as horses and companion animals such as dogs and cats. Mammal, animal, subject and patient are used interchangeably in this invention.

In one embodiment, HMB is administered to a mammal after incurring soft tissue trauma. Soft tissue trauma includes acute trauma such as a muscle tear or rupture, or the acute trauma that occurs as a result of any surgical procedure that involves incising or manipulating soft tissue. Acute trauma includes but is not limited to Achilles tendon rupture or tear, anterior cruciate ligament rupture or tear, medial collateral ligament rupture or tear, elbow ligament tear, tendon tears, sprains, strains, rotator cuff tear, and shoulder injuries. Acute trauma also includes the acute trauma incurred from any surgical procedure that cuts or manipulates soft tissue, including orthopedic surgery, soft tissue repair surgery, cardiac surgery, gynecologic surgery, plastic surgery, bariatric surgery, shoulder surgery, elbow surgery, hand surgery, hip surgery, knee surgery, ankle surgery, and spine surgery.

In one embodiment of this invention, HMB is administered to a mammal after sustaining any non-acute soft tissue injury. Non-acute soft tissue trauma includes but is not limited to tendonitis, bursitis, carpal tunnel syndrome, and plantar fasciitis.

HMB is administered to the mammal after the soft tissue injury is sustained. By way of non-limiting example, HMB is administered to an animal from around the time a surgery occurs. HMB administration continues until the mammal substantially recovers from the surgery or is released by a medical professional. Medical professionals include but are not limited to physicians, veterinarians, physical therapists, physician's assistants and nurse practitioners.

In the instance of soft tissue trauma that is unrelated to surgery, administration of HMB begins at any time after the trauma is incurred and continues until the mammal has a substantially complete recovery or is released by a medical professional.

The present invention also includes instances wherein a mammal incurs a soft tissue injury that subsequently requires surgical repair. The present invention includes instances wherein HMB is administered after the initial soft tissue injury and continues after the subsequent surgical repair during recovery from the surgery. It also includes instances wherein HMB is only administered after the surgical procedure and not in the period of time between when the soft tissue injury occurred and the surgical procedure takes place.

The present invention can be given to an individual during the pre- and post-operative or pre- and post-procedure period (the "peri-operative period"). In one embodiment, the composition is administered prior to the operation or procedure and administration continues for a period of time after the operation or procedure. The peri-operative period may include days, weeks or months after the surgery has occurred.

The enhanced recovery following soft tissue injury includes a reduced recovery time. Administering HMB in the manner described herein results in a reduced recovery time wherein the reduction in recovery time includes fewer days to reach substantially complete recovery or release from a medical professional than the recovery time of a mammal not taking HMB.

HMB

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. Derivatives include metabolites, esters and lactones. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. (1958) in which the free acid of HMB is neutralized with calcium hydroxide and recovered by crystallization from an aqueous ethanol solution. The calcium salt of HMB is commercially available from Metabolic Technologies, Ames, Iowa.

Calcium β-hydroxy-β-methylbutyrate (HMB) Supplementation

Numerous studies have shown that CaHMB supplementation improves muscle mass and strength gains in conjunction with resistance-exercise training, and attenuates loss of muscle mass in conditions such as cancer and AIDS. Nissen and Sharp performed a meta-analysis of supplements used in conjunction with resistance training and found that HMB was one of only two supplements that had clinical studies showing significant increases in strength and lean mass with resistance training. Studies have shown that 38 mg of CaHMB per kg of body weight appears to be an efficacious dosage for an average mammal.

In addition to strength and muscle mass gains, CaHMB supplementation also decreases indicators of muscle damage and protein degradation. Human studies have shown that muscle damage following intense exercise, measured by elevated plasma CPK (creatine phosphokinase), is reduced with HMB supplementation. The protective effect of HMB has been shown to manifest itself for at least three weeks with continued daily use. In vitro studies in isolated rat muscle show that HMB is a potent inhibitor of muscle proteolysis especially during periods of stress. These findings have been confirmed in humans; for example, HMB inhibits muscle proteolysis in subjects engaging in resistance training.

The molecular mechanisms by which HMB decreases protein breakdown and increases protein synthesis have been reported. Eley et al conducted in vitro studies which have shown that HMB stimulates protein synthesis through mTOR phosphorylation. Other studies have shown HMB decreases proteolysis through attenuation of the induction of the ubiquitin-proteosome proteolytic pathway when muscle protein catabolism is stimulated by proteolysis inducing factor (PIF), lipopolysaccharide (LPS), and angiotensin II. Still other studies have demonstrated that HMB also attenuates the activation of caspases-3 and -8 proteases. Taken together these studies indicate that HMB supplementation results in increased lean mass and the accompanying strength gains through a combination of decreased proteolysis and increased protein synthesis.

HMB Free Acid Form

In most instances, the HMB utilized in clinical studies and marketed as an ergogenic aid has been in the calcium salt form. Recent advances have allowed the HMB to be manufactured in a free acid form for use as a nutritional supplement. Recently, a new free acid form of HMB was developed, which was shown to be more rapidly absorbed than CaHMB, resulting in quicker and higher peak serum HMB levels and improved serum clearance to the tissues.

HMB free acid may therefore be a more efficacious method of administering HMB than the calcium salt form, particularly when administered directly preceding intense exercise. HMB free acid initiated 30 min prior to an acute bout of exercise was more efficacious in attenuating muscle damage and ameliorating inflammatory response than CaHMB. One of ordinary skill in the art, however, will recognize that this current invention encompasses HMB in any form.

The HMB itself can be present in any form; for example, CaHMB is typically a powder than can be incorporated into any delivery form, while HMB-acid is typically a liquid or gel that can be incorporated into any delivery form.

HMB in any form may be incorporated into the delivery and/or administration form in a fashion so as to result in a typical dosage range of about 0.5 grams HMB to about 30 grams HMB. HMB can also be present in a dosage range of 0.001 to 0.2 grams of HMB per kilogram body weight. HMB can be administered to the animal in multiple servings per day or a single serving.

Non-limiting examples of delivery forms include pills, tablets, capsules, gelcaps, liquids, beverages, solids and gels. Non-limiting examples of oral formulations that may be used to administer the composition of the present invention include a nutritional formulation, a medical food, a medical beverage, a sports performance supplement, a meal, or a food additive.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, vitamins (including but not limited to Vitamin D), minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water.

The composition of the dietary supplement may be a powder, a gel, a liquid or may be tabulated or encapsulated.

Although any suitable pharmaceutical medium comprising the composition can be utilized within the context of the present invention, the composition can be combined with a suitable pharmaceutical carrier, such as dextrose or sucrose.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, peptides, proteins and/or lipids. The amounts of the composition to be administered intravenously can be similar to levels used in oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). HMB can be administered over an extended period of time, such as weeks, months or years.

Any suitable dose of HMB can be used within the context of the present invention. Methods of calculating proper doses are well known in the art.

In general, an amount of HMB in the levels sufficient to result in enhanced or improved recovery from soft tissue injuries or trauma are provided.

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

Case Study 1

A healthy 39 year old male presented for Ruptured Achilles Repair of the left leg. Rupture of the Achilles tendon occurred three days prior to surgery. The surgeon conducting the repair had approximately fifteen years of experience at the time of the surgery.

After the surgery, Nucynta (50 mg tabs, 1-2 tabs every 4-6 hours) and Hydrocodone/Acetaminophen (5 mg/500 mg per tablet, 1-2 tabs every 4-6 hours) were taken for three days. This pain relief regime is typical for this type of surgery.

HMB was taken from the day of surgery through approximately four months after surgery. Three grams of calcium HMB were taken per day with normal diet.

Immediately following surgery, the leg was casted and use of crutches was required. The leg was re-casted approximately fourteen days later. The physician noted at the time of recasting that the strength and range of motion were above average. The second cast was removed approximately fourteen days later (four weeks post-surgery) and strength and range of motion continued to be ahead of the physician's schedule. Following the cast removal, a Bledsoe Boot was used to protect and limit leg range of motion with "wedges" under the heel. A cane was required. At the follow-up appointment approximately one month later, the recovery continued to be ahead of schedule with improved range of motion. No wedging was required at this point, and a cane was required for activity outside of the home. At a follow-up visit approximately one month later, the boot was required only during activity outside of the home and starting 2-3 weeks later, patient could resume normal physical activity if no pain or weakness was experienced.

Subject was cleared for all activity approximately six weeks after the second follow-up visit, which was approximately four months after surgery. No further doctor visits or therapy was required. In this case, no therapy was prescribed as physical ability had recovered completely by the final doctor visit. The patient returned to normal physical activity approximately three and half months after surgery, including walking, lifting weights and normal daily activity. The surgeon commented that the patient's recovery was the fastest recovery for his practice to date; the patient set the new record for the quickest recovery of an Achilles Rupture Repair.

This case study patient's recovery is compared to a typical recovery as follows. For a typical Achilles Rupture Repair, after surgery the patient will likely wear a cast, walking boot or similar device for six to twelve weeks. At first, the cast or boot is positioned to keep the foot pointed downward as the tendon heals. The cast or boot is then adjusted gradually to put the foot in a neutral position (not pointing up or down). Many health professionals recommend starting movement and weight-bearing exercises early, before the cast or boot comes off. Total recovery time is typically six months.

Case Studies 2-3
Participants

To test the effectiveness of HMB during ACL rehabilitation, pilot data was collected at Iowa State University. Participants were recruited from Theilen Student Health Center in Ames, Iowa if they were healthy individuals between the ages of 18 and 49, had ACL reconstructive surgery in the past 4 months using a patella or semitendinosus graft, and were regularly attending physical therapy. Subjects were excluded if they have multiple or bilateral ligament tears, other health conditions preventing regular engagement of physical therapy or that effect muscle atrophy, or were NCAA student athletes. After clearance from a medical provider, three participants came in for baseline measurements during an initial visit and were randomly assigned to HMB or placebo supplementation for 8 weeks before returning to our lab for final measurements. One participant withdrew from the study due to time constraints, so data was collected from one male and one female.

Supplementation

Both participants were randomly assigned to 8 weeks of HMB supplementation. The supplements were supplied by Metabolic Technologies (Ames, Iowa, USA), and distributed in capsule form, identical in size, color, and appearance. The HMB capsules each contained 0.5 g of HMB. Throughout the intervention, participants will be expected to consume 3 supplements in the morning with breakfast and 3 in the afternoon with dinner, for a daily total of 3 g. Participants documented any missed supplements on an adherence log to measure compliance.

Outcome Measures
KOOS Questionnaire:

Each participant completed a Knee Injury and Osteoarthritis Outcome Score (KOOS) questionnaire to evaluate overall knee functionality. The KOOS is a valid and reliable instrument used to measure perceived functional differences in knee integrity (Roos & Lohmander, 2003). This questionnaire investigates: level of pain (nine items); other symptoms, such as swelling, range of motion, or mechanical symptoms (seven items); function in daily living (17 items); function of sport and recreation (five items); and knee-related quality of life (four items). A Likert scale was used to gather information regarding each item, with zero indicating No Problems and four indicating Extreme Problems. These responses are then used to determine a score from 0 to 100 for each domain, in which 0 represents Extreme Knee Problems and 100 represents No Knee Problem. This evaluation measured differences of perceived knee functionality between initial to final testing.

Mid-Thigh Girth:

Mid-thigh girth measurements were obtained from both lower extremities using a standard circumferential measuring tape, pre and post supplementation. Mid-thigh sites are determined using the midpoint of the inguinal crease and the proximal border of the border of the patella. Three measurements were taken for each limb, rounding to the nearest 0.1 cm, and the average was recorded. Mid-thigh girth measurements are reliable methods of quantifying size differences in lower extremities following ACL reconstructive surgery (Soderberg, Ballantyne, & Kestel, 1996).

Lean Body Mass:

The InBody 720 was used to measure differences in muscle mass between the involved and non-involved limb. To begin, height was rounded to the nearest 0.1 cm as the participants stand against a stadiometer. Body mass was assessed using the scale on the InBody 720, measured to the nearest 0.1 kg. Prior to the impedance measure, sex, age, and height were manually entered. Once entered, participants were instructed to place their bare feet on the metal plates of the scale and firmly grasp the hand grips by placing their thumbs on the thumb plates and grasping the other plate with their other fingers, as indicated on the operation manual to begin the assessment. Once completed, the InBody 720 printed out a report consisting of impedance measurements for each frequency and estimates of FFM for all 5 segments, including left arm, right arm, torso, left leg, and right leg. Bioelectrical impedance is a reliable and valid tool for measuring body composition (Hurst et al, 2015).

Y Balance Functionality Test:

The Y balance test was used to assess functional deficits of the involved limb. Anterior, posteromedial, posterolateral measurements of the involved and non-involved were taken three times, recording the average. The Y Balance test is a reliable and valid tool, commonly used in rehabilitation to assess functional ability. In previous investigations, deficits using this tool identified individuals that did not meet rehabilitation goals and were delayed in returning to regular activity levels (Harrison, Bothwell, Wolf, Aryal, & Thigpen, 2015).

Results

Female Case Study

The first participant was a 22-year-old female, who ruptured her left ACL after falling while skiing. The participant underwent surgery 12 weeks prior to being enrolled in the study. Participant characteristics are summarized below in Table 1. Initial lean body mass of the involved leg was 5.6 kg and decreased to 5.5 kg after 8 weeks of supplementation. The non-involved limb remained unchanged at 5.5 kg throughout this investigation. Mid-thigh girth measures increased from 47.5 cm to 49.2 cm, reducing the deficit of the involved leg to the un-involved leg from 3.65% to 1.4%. Averages on the involved leg for each movement of the Y Balance Test are shown in Table 2. Both the involved and involved limbs improved from initial to the final visit, and the involved to non-involved deficit decreased from 4.4 cm at the initial to 2 cm at the final for anterior movement. Finally, pre and post results from the KOOS questionnaire are shown in FIG. 1 (scores are percentages, with 100% indicative of No Knee Problems and 0% indicating Extreme Knee Problems). Perception of pain, symptoms, and activities of daily life all increased (ie, improved).

TABLE 1

| Participant Characteristics | |
|---|---|
| Height (cm) | 151 |
| Weight (kg) | 59.2 |
| Lean Body Mass (kg) | 37.8 |
| Fat Mass (kg) | 21.4 |
| Body Fat (%) | 36.1 |

TABLE 2

| Initial and Final Y Balance Test Results | | |
|---|---|---|
| Y Balance Test Direction | Initial | Final |
| Anterior (cm) | 46.6 | 49.3 |
| Posterior-Medial (cm) | 80 | 81 |
| Posterior-Lateral (cm) | 80.3 | 83.3 |

Male Case Study

The second participant was a 22-year-old male, who ruptured his ACL when landing from a lay-up while playing basketball. He underwent surgery utilizing a semitendinosus tendon graft less than a month after injuring his knee, and was enrolled in the study 12 weeks after. Participant characteristics are summarized in Table 3. Lean body mass of the injured limb increased from 8.4 kg to 8.6 kg, and the un-injured limb increased from 8.5 kg to 8.7 kg. Girth measures were also slightly increased from 49.2 cm to 50.1 cm. Y Balance Test scores were averaged and are shown in Table 4. While the posteromedial and posterolateral movements remained similar, the deficit of involved to noninvolved for anterior movement was decreased from 4 cm to 1.7 cm.

Figure 2:
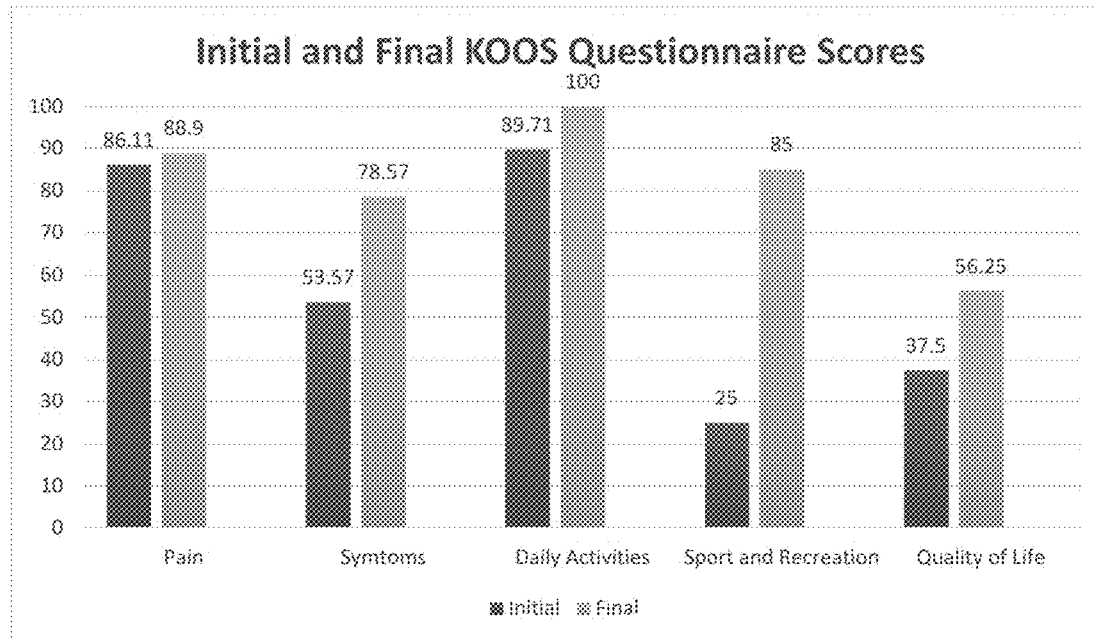
FIG. 2 is a graph depicting the initial and final KOOS Questionnaire Scores for the male subject.

Finally, KOOS questionnaire scores are shown on FIG. 2 (scores are percentages, with 100% indicative of No Knee Problems and 0% indicating Extreme Knee Problems). All areas of perception of function increased, with the greatest improvement in sport/recreational activities and overall quality of life.

TABLE 3

| Male Participant Characteristics | |
|---|---|
| Height (cm) | 170 |
| Weight (cm) | 71.9 |
| Lean Body Mass (kg) | 55.3 |
| Body Fat Mass (kg) | 16.6 |
| Body Fat (%) | 23 |

TABLE 4

| Initial and Final Y Balance Test Results | | |
|---|---|---|
| Y Balance Test Direction | Initial | Final |
| Anterior (cm) | 53.6 | 64.6 |
| Posterior-Medial (cm) | 100 | 104 |
| Posterior-Lateral (cm) | 97 | 104 |

Analysis

Both participants increased mid-thigh girth, functionality assessed by the Y Balance test, and perceived functionality assessed by the KOOS questionnaire.

Experimental Example

Fifteen female New Zealand White rabbits (43 weeks old) (Covance Research Products, Inc., Greenfield, Ind.) were used in the 8-week study conducted at the University of Calgary (Calgary, Alberta, Canada). Botox was used as an agent to replicate soft tissue trauma.

The rabbits were randomly assigned to one of the following treatment groups:

(1) Control group: saline injection unilaterally (n=5);
(2) Botox group: single Botox injection unilaterally (n=5);
(3) Botox+HMB group: single Botox injection unilaterally+CaHMB food supplementation throughout the experimental period (n=5). HMB=Calcium salt of β-hydroxy-β-methylbutyrate Group 1 rabbits served as controls and received intramuscular saline injection randomized (right or left) to the quadriceps musculature. The total volume of injected saline was the same as the total volume of Botox. Groups 2 and 3 rabbits received a one-time intramuscular Botox injection and data was collected eight weeks following the injection.

Botox Injections: The rabbits in the saline group were injected with 0.175 ml saline/kg body weight. The rabbits in the Botox and Boxtox+HMB groups were injected with a *Clostridium botulinum* type-A (BTX-A) neurotoxin complex (Botox®, Allergan, Inc. Toronto, Ontario, Canada). Briefly, the lyophilized toxin (100 U/vial) was reconstituted with 0.9% sodium chloride to a concentration of 20 U/ml. The right or left leg was chosen at random and 3.5 U/kg body weight was injected into the quadriceps muscle. The anterior compartment of the thigh was isolated by palpation and the quadriceps muscle visually divided into superior and inferior halves. Each half was then each subdivided into a medial, lateral, and central section. One sixth of the BTX-A dose was injected into each section to increase the diffusion and to equally distribute the BTX-A through the quadriceps musculature.(5; 6)

Diet: Group 1 and 2 rabbits received a high fiber diet (Laboratory Rabbit Diet HF 5326, LabDiet, Richmond, Ind.), while group 3 rabbits received the same base diet custom formulated with 0.44% CaHMB (Metabolic Technologies, Inc., Ames Iowa, USA). Body weights and feed intakes were recorded weekly.

Quadriceps Muscle Mass: Following the 8-week feeding period, the rabbits were killed by an overdose of Euthanyl (MTC Pharmaceutical, Cambridge, Ontario, Canada) given into the heart. The wet muscle mass of the quadriceps muscle was then immediately determined. The quadriceps muscle group was removed and the rectus femoris (RF), vastus medialis (VM), and vastus lateralis (VL) were separated and individually weighed using a commercial scale with an accuracy of 0.01 g.

Statistical Analysis

The data were analyzed using Proc GLM in SAS (SAS for Windows 9.4, SAS Institute, Inc., Cary, N.C.). The model used the main effect of treatment. For actual muscle weights, body weight of the rabbit was used as a covariate. Means reported are Least Squares means and the standard error of the mean was calculated from the mean square of the error term of the main effect model. The p-values given for overall treatment are from the main effect model while individual means were compared using the Least Square Means predicted difference. A p-value≤0.05 indicates significance while 0.05<p<0.10 indicates a definite trend towards significance in the data.

TABLE 5

Least Squares Means of muscle mass for injected and contralateral non-injected from control, Botox, and Botox + HMB group rabbits.[a]

| | Injected Leg | | | | | Contralateral Leg | | | | |
|---|---|---|---|---|---|---|---|---|---|---|
| | Control | Botox | Botox + HMB | SEM | P | Control | Botox | Botox + HMB | SEM | P |
| Vastus lateralis | 17.6 | 7.8 | 7.8 | 0.40 | 0.0001 | 18.1 | 18.0 | 18.9 | 0.31 | 0.45 |
| Vastus medialis | 5.2 | 4.1 | 4.4 | 0.18 | 0.10 | 5.3 | 5.0 | 5.4 | 0.20 | 0.19 |
| Rectus femoris | 9.8 | 6.9 | 5.8 | 0.35 | 0.002 | 10.2 | 10.3 | 11.1 | 0.13 | 0.47 |
| Small vastus lateralis | 6.1 | 6.5 | 6.9 | 0.16 | 0.17 | 6.1 | 6.3 | 6.7 | 0.16 | 0.37 |
| Total Weight, g | 38.6 | 25.3 | 24.8 | 0.55 | 0.0001 | 39.7 | 39.6 | 42.1 | 0.48 | 0.10 |

[a] n = 5 per treatment. HMB was supplemented as calcium beta-hydroxy-beta-methylbutyrate mixed in the complete feed at 0.44% weight.

Results

Injection with botox resulted in an approximately 39% decrease in muscle size for all muscles measured. Only the small vastus lateralis muscle was not affected by the botox injection. The injected leg vastus medialis muscle was larger in the botox+HMB group than in the botox alone group and a t-test of least square means differences showed that only the botox group was significantly different from the control group (p<0.05). In addition, the injected leg small vastus lateralis muscle in the botox+HMB group tended to be larger than in the control group (p<0.07). Least square means analysis of the botox+HMB group rectus femoris muscle tended to be greater than the rectus femoris muscle weights in the control group (p<0.10). The total weight of the measured muscles in the contralateral leg for the botox+ HMB group were greater than those in the botox alone group (p<0.06) and tended to also be greater than the total weight of the muscles in the control group (p<0.07). Additionally, the muscles affected the most by the botox injection weighed more in the contralateral leg for the botox+HMB group than the botox group ($p<0.05$) and tended to be greater than in the control group ($p<0.10$). Expressing the muscle weights as a percentage of body weight showed the same effect, larger contralateral musculature with HMB versus the botox group ($p<0.07$) and the control group ($p<0.04$).

Supplementation with HMB helped to preserve muscle mass in the botox-injected rabbits. HMB greatly increased the muscle hypertrophy in the contralateral leg in the botox+HMB group when compared with both the botox and control groups. Thus, HMB did help preserve and hypertrophy muscles despite the severe nature of the botulinum toxin. This observation, coupled with the case studies demonstrate that HMB enhances recovery from soft tissue trauma and aids in the healing of soft tissues.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

The invention claimed is:

1. A method of enhancing recovery from acute soft tissue injury, comprising administering to a human in need thereof a composition comprising from about 0.001 to 0.2 grams of β-hydroxy-β-methylbutyric acid (HMB) per kilogram of body weight, wherein the HMB further comprises HMB in its free acid form, its salt, its ester or its lactone, and wherein soft tissue is selected from the list consisting of tendons, and ligaments.

2. The method of claim 1, wherein recovery from the soft tissue injury is improved relative to recovery from soft tissue injury in a human not administered said composition.

3. The method of claim 1, wherein said salt is selected from the group consisting of a sodium salt, a potassium salt, a magnesium salt, a chromium salt, and a calcium salt.

4. The method of claim 1, wherein the composition is administered in the amount of 0.5 g to 30 g.

5. A method of reducing recovery time from acute soft tissue injury, comprising administering to a human in need thereof a composition comprising from about 0.001 to 0.2 grams of β-hydroxy-β-methylbutyric acid (HMB) per kilogram of body weight, wherein the HMB further comprises HMB in its free acid form, its salt, its ester or its lactone and wherein soft tissue is selected from the list consisting of muscle, tendons, and ligaments.

6. The method of claim 5, wherein the recovery time is shorter for the human administered the composition relative to the recovery time in a human not administered said composition.

7. The method of claim 5, wherein said salt is selected from the group consisting of a sodium salt, a potassium salt, a magnesium salt, a chromium salt, and a calcium salt.

8. The method of claim 5, wherein the composition is administered in the amount of 0.5 grams to 30 grams.

9. The method of claim 5, wherein the composition is administered for a period of days, weeks or months subsequent to the soft tissue injury.

10. A method of improving healing from acute soft tissue injury, comprising administering to a human in need thereof a composition comprising from about 0.001 to 0.2 grams of β-hydroxy-β-methylbutyric acid (HMB) per kilogram of body weight, and wherein soft tissue is selected from the list consisting of tendons, ligaments.

11. The method of claim 10, wherein the soft tissue healing is improved for the human administered the composition relative to the soft tissue healing in a human not administered said composition.

12. A method of enhancing recovery from non-acute soft tissue trauma, comprising administering to an human in need thereof a composition comprising from about 0.001 to 0.2 grams of β-hydroxy-β-methylbutyric acid (HMB) per kilogram of body weight wherein the HMB further comprises HMB in its free acid form, its salt, its ester or its lactone, and wherein the non-acute trauma is selected from the list consisting of tendonitis, bursitis, carpal tunnel syndrome, and plantar fasciitis.

13. The method of claim 12, wherein the repair of the soft tissue trauma is improved for the human administered the composition relative to repair of the soft tissue trauma in a human not administered said composition.

14. The method of claim 1, wherein the acute injury is selected from the list consisting of surgery, Achilles tendon rupture or tear, anterior cruciate ligament rupture or tear, medial collateral ligament rupture or tear, elbow ligament tear, tendon tear, sprains, strains, rotator cuff tear and shoulder injuries.

15. The method of claim 1, wherein enhanced recovery further comprises healing, regeneration or repair of the soft tissue.

16. A method of reducing recovery time from surgery, comprising administering to a human about to undergo, undergoing or just having undergone surgery a composition comprising from about 0.001 to 0.2 grams of β-hydroxy-β-methylbutyric acid (HMB) per kilogram of body weight, wherein the type of surgery is orthopedic surgery, shoulder surgery, elbow surgery, hand surgery, hip surgery, knee surgery, ankle surgery, or spinal surgery.

17. A method for enhancing recovery in a surgical patient comprising administering to the patient a composition comprising from about 0.5 to about 30 grams of β-hydroxy-β-methylbutyric acid (HMB) wherein administration of the composition begins prior to surgery, during surgery or post-surgery and wherein the type of surgery is orthopedic surgery, shoulder surgery, elbow surgery, hand surgery, hip surgery, knee surgery, ankle surgery, or spinal surgery.

18. The method of claim 17, wherein enhanced recovery further comprises improved healing, regeneration or repair of soft tissue.

19. The method of claim 17, wherein recovery from surgery is improved relative to recovery from surgery in a patient not administered said composition.

20. The method of claim 17, wherein the HMB further comprises HMB in its free acid form, its salt, its ester or its lactone.

21. A method of expediting the repair or regeneration of soft tissue that has been subjected to acute injury comprising administering to a human in need thereof a composition comprising from about 0.5 to about 30 grams of β-hydroxy-β-methylbutyric acid (HMB), wherein the soft tissue is selected from the list consisting of tendons and ligaments.

* * * * *